US008640971B2

(12) United States Patent
Feriani et al.

(10) Patent No.: US 8,640,971 B2
(45) Date of Patent: Feb. 4, 2014

(54) NEBULIZER

(75) Inventors: Amir Feriani, Auvernier (CH); Joseph Hess, Bevaix (CH); Cédric Zaugg, Neuchâtel (CH)

(73) Assignee: EP Systems SA, Neuchâtel (CH)

( * ) Notice: Subject to any disclaimer, the term of this patent is extended or adjusted under 35 U.S.C. 154(b) by 557 days.

(21) Appl. No.: 12/624,355

(22) Filed: Nov. 23, 2009

(65) Prior Publication Data

US 2010/0219263 A1 Sep. 2, 2010

(30) Foreign Application Priority Data

Nov. 24, 2008 (EP) .................................... 08169784

(51) Int. Cl.
*B05B 1/08* (2006.01)

(52) U.S. Cl.
USPC ..................... 239/102.2; 239/102.1; 239/338; 128/200.14; 128/200.16

(58) Field of Classification Search
USPC ....................... 239/102.1, 102.2, 338, 370, 4; 128/200.14, 200.16
See application file for complete search history.

(56) References Cited

U.S. PATENT DOCUMENTS 4,410,139 A * 10/1983 Nishikawa et al. ......... 239/102.2
6,283,118 B1 * 9/2001 Lu ........................... 128/200.16
6,705,312 B2 3/2004 Tanaka et al.
7,779,831 B1 * 8/2010 Von Hollen et al. ..... 128/200.16

OTHER PUBLICATIONS

Capillary action, from USGS Water-Science School, at http://ga.water.usgs.gove/edu/capillaryaction.html (last modified Oct. 15, 2012), filed herewith as Exhibit A.

Capillary action, at http://www.thermopedia.com/content/31/ (Sep. 7, 2010), filed herewith as Exhibit B.

"Water Flowing (Discharging) from a Tank," at http://www.Imnoeng.com/TankDischarge.htm (last modified Sep. 2, 2008), filed herewith as Exhibit C.

Capillary Action, at http://chemwiki.ucdavis.edu/Physical_Chemistry/Physical_Properties_of_Matter/Intermolecular_Forces/Cohesive_And_Adhesive_Forces/Capillary_Action (downloaded Oct. 16, 2012).

J.A. Weibel et al., Characterization of Evaporation and Boiling from Sintered Powder Wicks Fed by Capillary Action, CTRC Research Publications (2010).

* cited by examiner

*Primary Examiner* — Jason Boeckmann
(74) *Attorney, Agent, or Firm* — Griffin & Szipl, P.C.

(57) ABSTRACT

A nebulizer comprising a main body, an atomizer, and a vibrating element. The atomizer comprises a substrate, a main recipient supported by the substrate for containing liquid and having surfaces delimiting the liquid reservoir, and a dosing reservoir arranged on the main recipient so as to delimit a predetermined amount of liquid to be expelled. The dosing reservoir comprises a hollow section defining the predetermined amount of liquid, a solid section, a central section, an orifice membrane plate, and a fluidic channel arranged in-between a bottom surface of the solid section and the flat top surface of the main reservoir so as to create a capillary communication between the hollow section and the orifice membrane plate.

14 Claims, 5 Drawing Sheets

NEBULIZER

This application claims priority from European Patent Application No. 08 169 784.9, filed Nov. 24, 2008, the entire disclosure of which is incorporated herein by reference.

FIELD OF THE INVENTION

The present invention relates to a nebulizer that is principally, but not exclusively, used for therapeutic purposes. A liquid, such as a medicament in liquid form, is nebulized by the nebulizer into a spray of fine droplets and a patient breathes in this spray of droplets for treatment purposes. Other uses may relate to air-freshening, aromatherapy and the like.

BACKGROUND OF THE INVENTION

A known nebulizer is described in the document U.S. Pat. No. 6,705,312. This device has a main body containing a vibrating element, electronic circuitry, and battery for powering the circuitry and the vibrating element. An atomizer is provided on top of the main body, and is suitably coupled to the electronic circuitry and the vibrating element to allow for atomization of liquid. Generally, a mouthpiece is further added to allow a patient to correctly receive the atomized spray of droplets through the mouthpiece. The atomizer comprises an orifice plate through which liquid is ejected. By powering the vibrating element, an ultrasonic sound wave is applied to the liquid and this liquid will contact the orifice plate so as to be expelled as a spray of droplets.

The atomizer comprises a main reservoir into which a liquid substance that is to be expelled as a spray of droplets is poured prior to use. A chamber lid containing the orifice plate is provided over the main reservoir.

The main body further comprises a dosing reservoir that is provided on the top surface of the main body, just below the atomizer. By filling the main reservoir with liquid, a specific predetermined dose of liquid may thus enter this dosing reservoir. This dosing reservoir fixes the amount of liquid to be expelled, and thus depends on the desired treatment.

The chamber lid will seal both the main reservoir and the dosing reservoir, and thus delimits these reservoirs from each other. The remaining liquid in the main reservoir can be used for further doses, and this main reservoir thus constitutes a buffer zone.

A similar device is manufactured and commercialized by Respironics® as a so-called adaptive aerosol delivery device.

In this device, again the dosing reservoir is formed on the top surface of the main body, and is filled by first filling a main reservoir so that the correct amount of liquid may then enter the dosing reservoir. A chamber lid, once fitted over the dosing reservoir and the main reservoir, delimits one from the other so that the correct amount of liquid is trapped in the dosing reservoir. By activating a vibrating element contained in the main body, the atomizer will atomize liquid contained in the dosing reservoir and this will be expelled as a spray of droplets.

Both of these prior art devices thus have a dosing reservoir on the top surface of the main body. As such, a correct size of the dosing reservoir may be accurately defined when fabricating the main body.

However, this dosing reservoir is integrated into the main body, and forms part of the top surface. As such, the top surface is not flat, so that it becomes difficult to correctly clean the dosing reservoir.

This is of course most important to avoid contamination of liquid, either by residues that stick to the dosing reservoir and to the vibrating element, or by mixture with a different liquid if the treatment is altered.

Further, in the case, for example, the described device is used as an aromatherapy device having a similar structure, the mix of essences should of course be avoided, so that here too it is important to correctly clean the dosing reservoir and the vibrating element to avoid undesired mixing or contamination.

The atomizer can be removed and cleaned, for example in a tub, but the main body containing the power supply and the electronic circuitry cannot be readily plunged into a cleaning solution for thorough cleaning.

Thus, correct cleaning is very difficult, if not impossible to achieve.

Furthermore, due to the particular arrangement, the nebulizer can only operate when held at a specific angle, either otherwise the device may not work, or liquid may spill out.

It is, therefore, an object of the present invention to provide an innovative nebulizer that overcomes the inconveniences and limitations presented by the prior art, and that allows to ensure correct cleaning of the dosing reservoir and the vibrating element, as well as of the rest of the device, in a simple manner.

It is another object of the present invention to provide such nebulizer that is inexpensive, partly disposable and easy to use.

SUMMARY OF THE INVENTION

Thus, the present invention concerns a nebulizer. In accordance with a first embodiment of the present invention, a nebulizer is provided that comprises: a main body (1); an atomizer (2) for atomizing a liquid so as to expel the liquid as a spray of droplets from the nebulizer; and a vibrating element (22, 23), wherein the atomizer comprises: a substrate (4), a main recipient (16) supported by the substrate for containing the liquid and having a bottom outer surface, a flat top inner surface and an outer wall (**16*a*) erecting from the top surface to delimit the main recipient, a dosing reservoir (18) arranged on the main recipient (16) for delimiting a predetermined amount of the liquid to be expelled, and having a upper surface (18*t*) and a wall (18*a*) extending downwards from the upper surface (18*t*) towards the main recipient (16), when assembled thereto, the dosing reservoir (18) comprises a hollow section (18*c*) defining the predetermined amount of liquid, a solid section (18*d*) extending downwards from the upper surface (18*t*), a central section (18*e*) being a hole traversing the upper surface (18*t*) and arranged in the solid section (18*d*), an orifice membrane plate (22) arranged at the bottom of the hole of the central section (18*e*), for sealing the hole, and a fluidic channel (21) arranged in-between a bottom surface of the solid section (18*d*) and the flat top inner surface of the main recipient (16) for creating a capillary communication between the hollow section (18*c*) and the orifice membrane plate (22**).

In accordance with a second embodiment of the present invention, the first embodiment is modified so that the dosing reservoir has a top sealing surface (18-1) arranged above the fluidic channel (21) so that the fluidic channel (21) is trapped between the top surfaces (18-1) and a top surface of the vibrating element. In accordance with a third embodiment of the present invention, the first embodiment or the second embodiment is further modified so that the dosing reservoir (18) is provided as a disposable part. In accordance with a fourth embodiment of the present invention, the main recipient (16) is provided as a disposable part. In accordance with a fifth embodiment of the present invention, the first embodiment, the second embodiment, the third embodiment, and the fourth embodiment are further modified so that the main body (1) comprises electronic circuitry, the vibrating element (22, 23), and a power source for powering the vibrating element so as to act on liquid in the atomizer, whereby the liquid is expelled as a spray of droplets.

In accordance with a sixth embodiment of the present invention, the first embodiment, the second embodiment, the third embodiment and the fourth embodiment are modified so that the nebuliser (2) includes the vibrating element (22, 23), and the main body (1) includes a power source for powering the vibrating element so as to act on liquid in the atomizer, whereby the liquid is expelled as a spray of droplets.

Thanks to the features of the nebulizer according to the present invention, it is possible to reliably clean the dosing reservoir, as well as the main reservoir. The main reservoir and the vibrating element each have a bottom surface that is flat, and the dosing reservoir is of the disposable type.

BRIEF DESCRIPTION OF THE DRAWINGS

Other features and advantages of the nebulizer according to the present invention will become clear from reading the following description, which is given solely by way of a non-limitative example thereby referring to the attached drawings in which.

DETAILED DESCRIPTION OF THE INVENTION

An example of a preferred embodiment will now be described while referring to the figures.

Figure 1A:
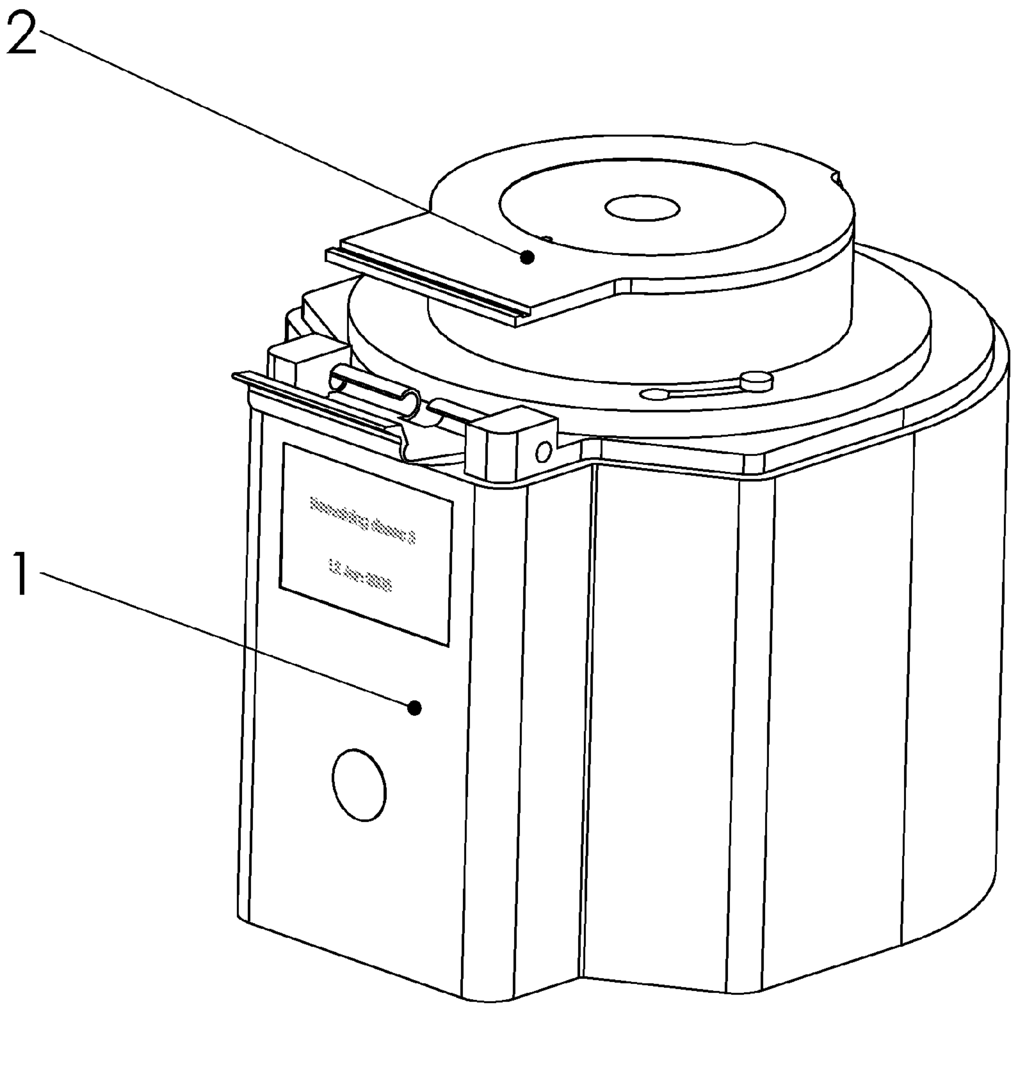
FIG. 1*a* and FIG. 1*b* show an example of a nebulizer according to the present invention.
Figure 1B:
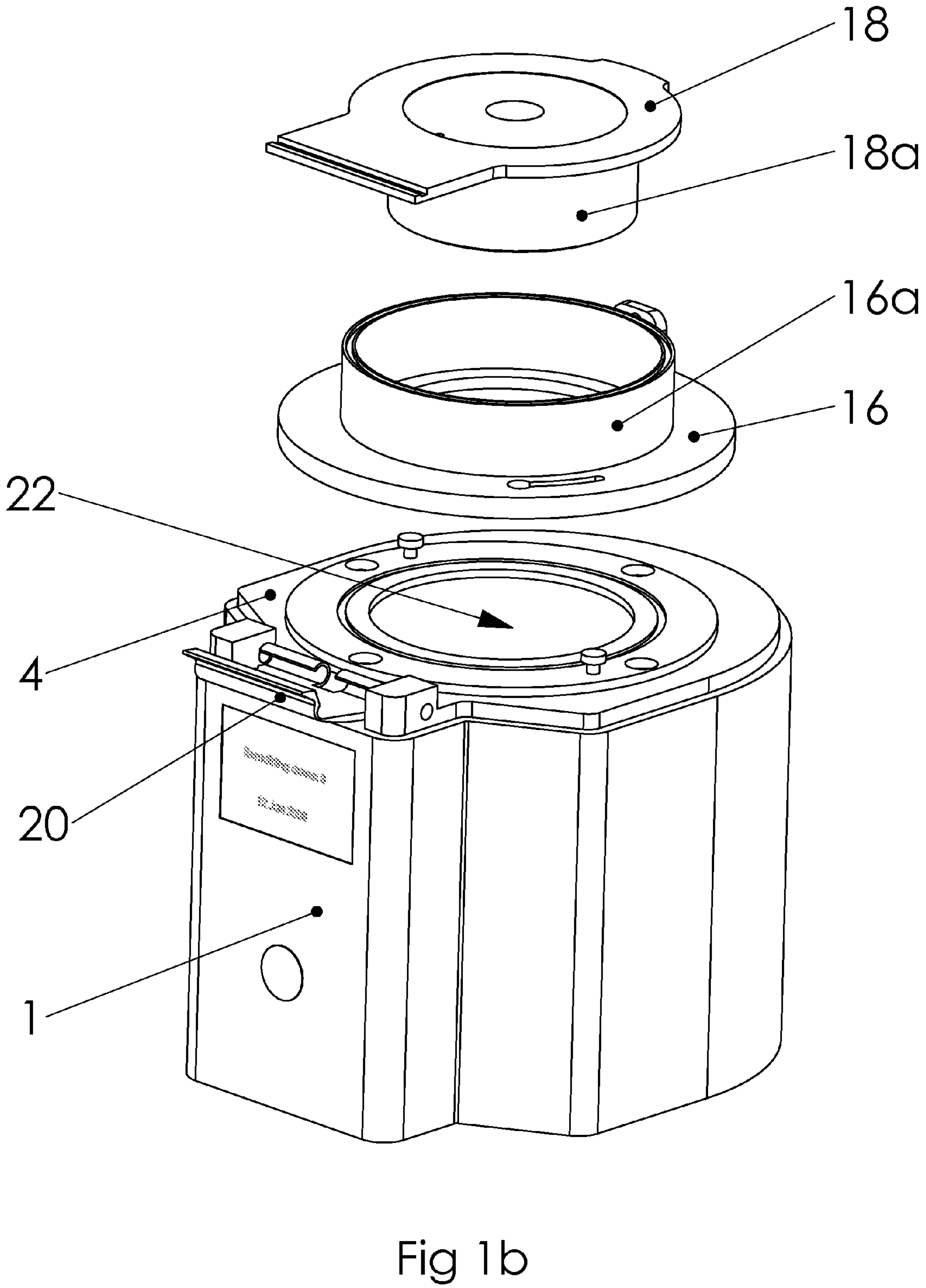

FIGS. 1*a* and 1*b* thus show a general overview of a nebulizer according to the present invention. The nebulizer has a main body 1 containing electronic circuitry and a battery for powering the circuitry, in a similar manner as in the conventional devices discussed here before. An atomizer 2 is provided on top of the main body, and is suitably coupled to the electronic circuitry, not shown, to allow for atomization of liquid. Generally, a mouthpiece, not shown, may be added allowing a patient to correctly receive the atomized spray of droplets through the mouthpiece.

Thus, the nebulizer comprises a vibrating element. This vibrating element may be included in the atomizer 2, which further comprises an orifice plate through which liquid is ejected. However, the vibrating element may also be arranged in the main body 1 instead of in atomizer 2. By powering the vibrating element, an ultrasonic sound wave is applied to the liquid and this liquid will contact the orifice plate so as to be expelled as a spray of droplets. In this example, the vibrating element may comprise an ultrasound transducer 23, such as a piezoelectric element, combined with a membrane plate 23 that is arranged so as to transmit ultrasonic energy generated by the ultrasound transducer to the liquid. Such membrane plate is optional.

In this embodiment, the atomizer comprises a main recipient into which a liquid substance that is to be expelled as a spray of droplets may be poured prior to use. A lid is provided over the main recipient. According to the present invention, this lid is in the form of a dosing reservoir containing the orifice plate, as will be explained in more detail later.

Main body 1 is arranged to receive a flat substrate 4 for receiving the main recipient 16 and the dosing reservoir 18 (FIG. 1*b*).

Figure 2:
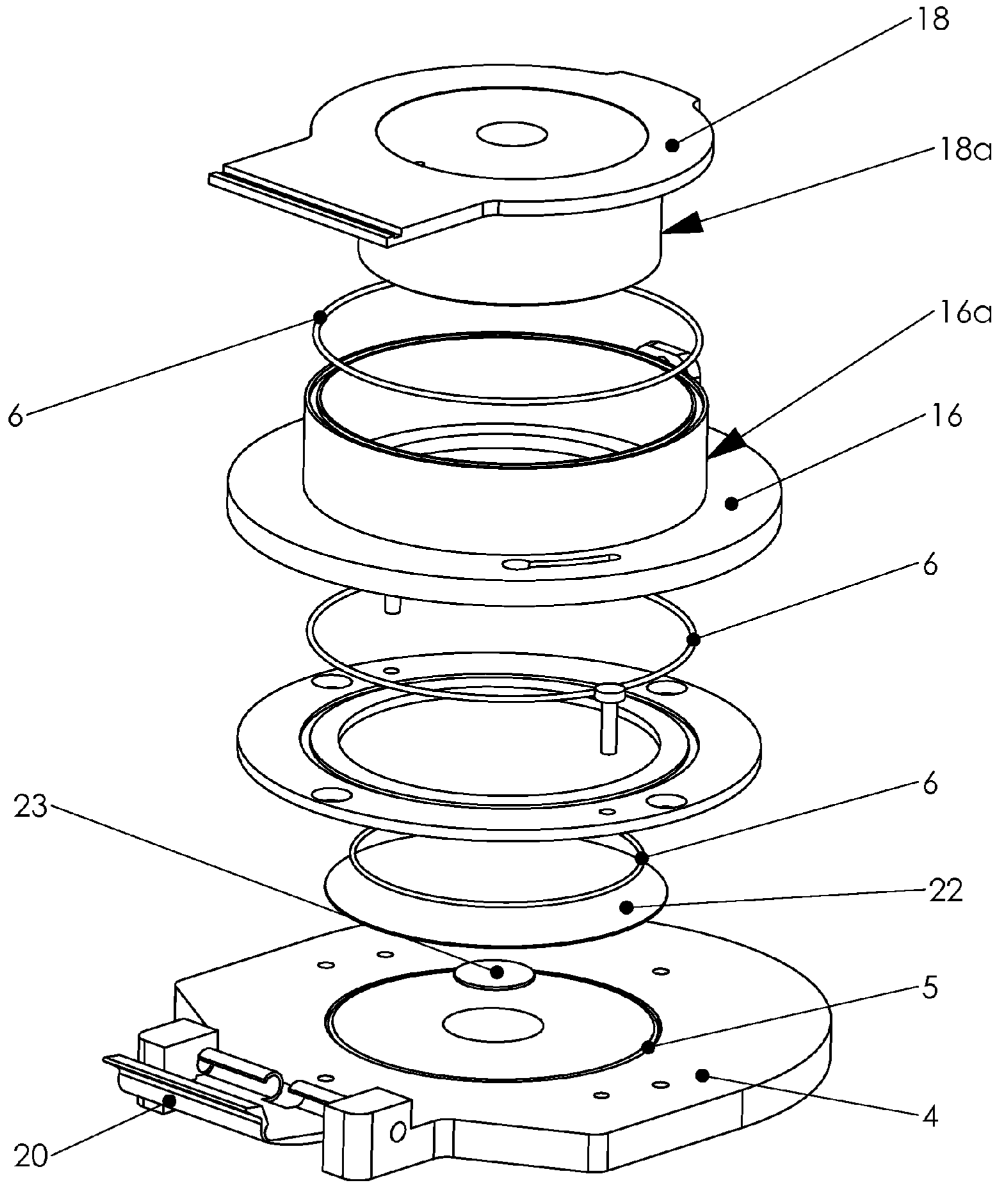
FIG. 2 shows an exploded view of an atomizer for a nebulizer according to the present invention.

As shown in FIG. 2, atomizer 2 comprises a bottom flat substrate 4, a main recipient 16 and a dosing reservoir 18 with, in this example, the flat substrate 4 being mounted on the main body 1 (not shown) and on the lower surface of this substrate 4 electrical connection pins may be provided for connection to the vibrating element and the electronics. Several other parts are provided to maintain the vibrating elements 22, 23 on the top surface of flat substrate 4.

Next, a main recipient 16 is provided and may receive liquid to be atomized. Main recipient 16 has a lower surface with a flat outer bottom surface, and a flat upper inner surface on which a wall 16*a* erects for delimiting the main recipient. Further, a dosing reservoir 18 is provided on the main recipient and may enter therein, in a manner as will be explained in more detail later. Several gaskets 6 are used to assure the sealing between the main recipient 16, dosing reservoir 18 and the top substrate 4.

Finally, the atomizer comprises an orifice membrane plate 22 through which liquid is ejected. Membrane plate 22 is arranged within dosing reservoir 18, as will be explained in more detail further on. By powering the vibrating element, an ultrasonic sound wave is applied to liquid contained in the dosing reservoir and this liquid will contact the orifice plate so as to be expelled as a spray of droplets.

As shown in this example, dosing reservoir 18 has a flat top surface 18*t* having a side projection that extends from its top surface 18*t* and that corresponds to and aligns with a side projection on substrate 4. A clip 20 may be fitted over these side projections to fix onto top surface 18*t* of dosing reservoir 18 so as to seal all elements together to ensure liquid-tightness of the atomizer. Such clip is known as such, and may be similar to that used in the Respironics® device discussed above. Of course, other suitable conventional attachment means may be used instead.

Dosing reservoir further has a wall 18*a* extending downwards from the top surface 18*t*, towards main recipient 16, when assembled thereto. The edge of top surface 18*t* may be partly provided with a rim, as can be seen in FIG. 3.

Figure 3:
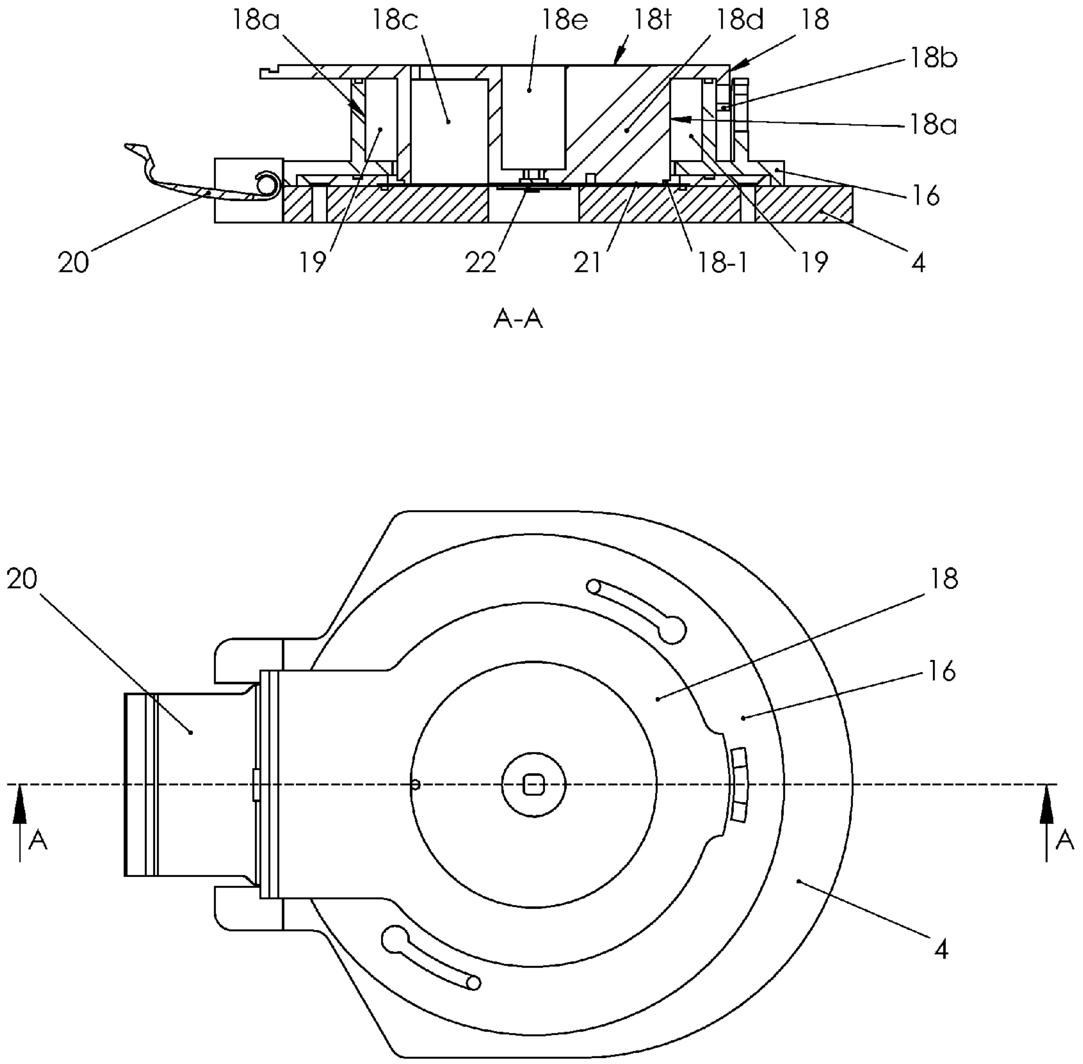
FIG. 3 shows a top view and a cross-sectional view of the assembled atomizer of FIG. 2.

FIG. 3 shows the atomizer in assembled state. Clip 20 fastens together dosing reservoir 18 to substrate 4, which together enclose main recipient 16. As can be seen, wall 16*a* of main recipient 16 has, in this example, a double-wall structure along a certain peripheral section with a groove therein for receiving rim 18*b* of the dosing reservoir to ensure correct sealing when these parts are fitted together.

Of course, other suitable arrangements may be conceived that allow for correct sealing of the main recipient and the dosing reservoir so that a predetermined amount of liquid is obtained when using the dosing reservoir of this embodiment.

Dosing reservoir 18 has a peripheral wall 18*a*, radially positioned inwards with respect to rim 18*b*, that fits into the inner part of main recipient 16 as delimited by wall 16*a*. As shown, wall 18*a* of the dosing reservoir is smaller in diameter than wall 16*a*, whereby a buffer zone 19 is created in main recipient 16, once the two parts are fitted together, as any remaining liquid in the main recipient, which is called the excess dose, cannot enter dosing reservoir 18 and may thus be used for further doses.

As such, a predetermined dose of liquid is trapped in dosing reservoir 18. Thus, in this embodiment, by filling the main recipient with liquid, a specific predetermined dose of liquid may enter this dosing reservoir. This dosing reservoir fixes the amount of liquid to be expelled, and thus its size depends on the desired treatment.

Figure 4:
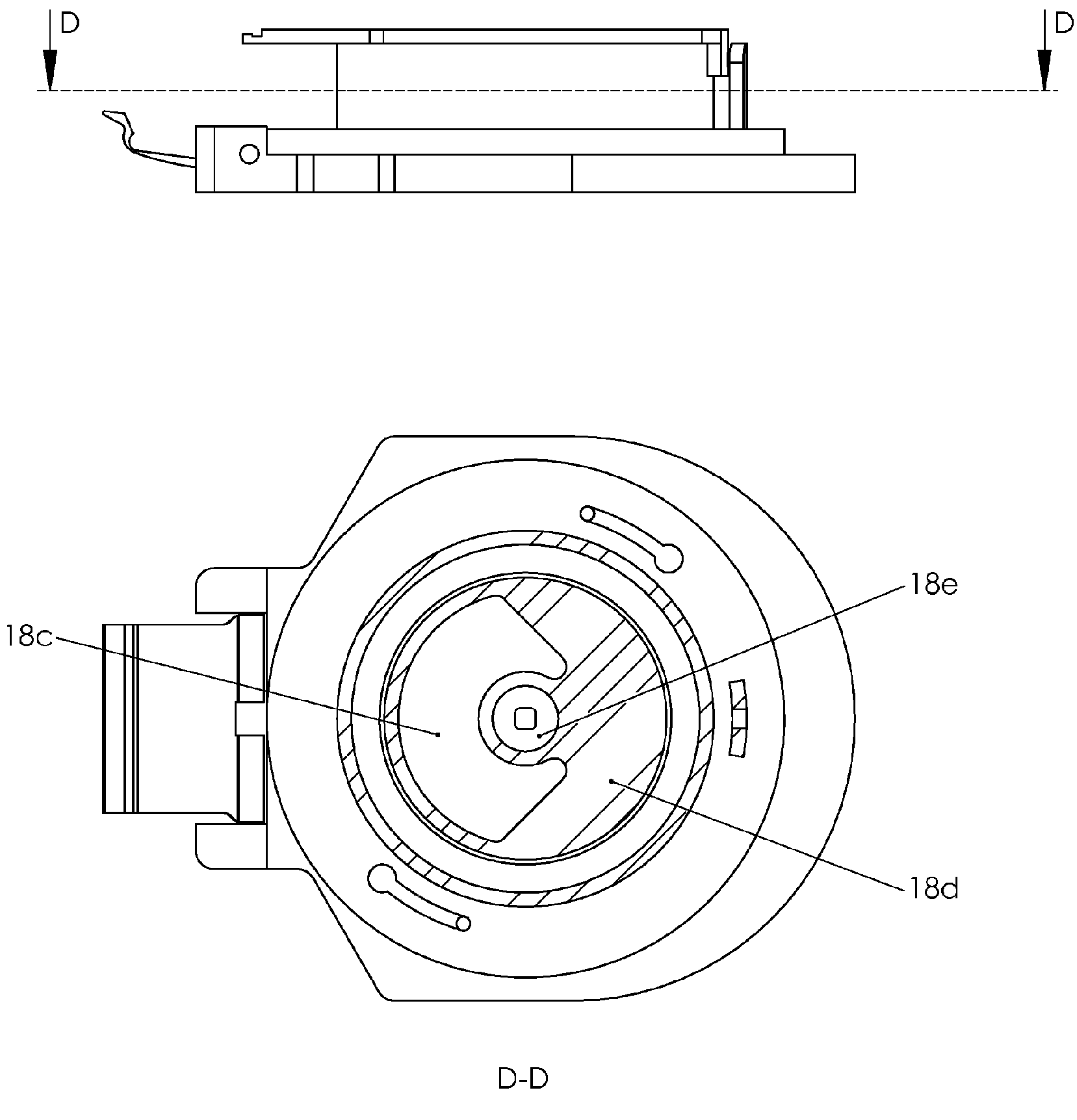
FIG. 4 shows a bottom view and a cross-sectional view of a disposable part of the atomizer of FIG. 2 comprising a dosing reservoir together with an orifice plate.

Dosing reservoir 18 will now be described in more detail with reference to FIGS. 3 and 4.

As can be seen, when looked upon from below, dosing reservoir 18 thus has top surface 18*t*, a hollow section 18*c*, a central section 18*e* and a solid section 18*d*. Hollow section 18*c* thus defines the actual dose of liquid to be expelled, as this section will be filled with liquid contained in main recipient 16 once the dosing reservoir is fitted thereon. Central section 18*e* is a hole traversing the top surface 18*t* and arranged in solid section 18*d* by removal of the material constituting dosing reservoir 18 in its centre portion. Orifice membrane plate 22 is arranged at the bottom of this hole of central section 18*e*, and thus seals this hole. Solid section 18*d* extends from the top surface of dosing reservoir downwards, similar to peripheral wall 18*a*. However, solid section 18*d* does not extend as far as wall 18*a*, but stops short thereof. Once assembled, this arrangement will create a fluidic channel 21 in-between the surface of solid section 18*d* and the flat surface of main recipient 16. This fluidic channel 21 allows for capillary communication between hollow section 18*c* and the centre portion of dosing reservoir 18 so that liquid may flow from the hollow section to the centre portion, and thus to the orifice membrane plate of dosing reservoir 18.

Orifice membrane plate 22 is arranged such that by powering the vibrating element, an ultrasonic sound wave is applied to the liquid and this liquid will contact the orifice plate so as to be expelled as a spray of droplets.

As can be understood from the above, as the inner surface of main recipient 16 is flat, it is easy to correctly clean such.

Further, this main recipient 16 can be easily removed from the main body, to allow for more thorough cleaning. Main body 1 does not itself enter into contact with any liquid, so it is not necessary to clean such, other than for normal maintenance.

In a further preferred arrangement, dosing reservoir 18, together with membrane plate 22 integrated therein, may be configured as a disposable part. This further avoids any risk of contamination, as simply the entire dosing reservoir and the membrane plate may be replaced after use. For example, every day, a patient merely attaches a new dosing reservoir with integrated membrane plate onto the main recipient for a next dose.

As such, it is also easier to allow for modified amounts of doses of liquids to be expelled. A set of dosing reservoirs may be provided, each with a different size of hollow section 18*c*, so that different predetermined doses, for different treatments, may be provided.

Advantageously, main recipient 16 may also be disposable to further avoid any risk of contamination.

The above arrangement further allows for an increased ease of use during operation of the device. In fact, due to the construction with orifice plate arranged in dosing membrane, and with the fluidic capillary channel there below, a pressure chamber is created below orifice plate. Any liquid entering this pressure chamber will be expelled as a spray of droplets once the vibrating element is powered.

This pressure chamber has as additional advantage that liquid contained in the dosing reservoir will not flow out of the atomizer when inclined, of course also by a suitable choice the size of the orifices in the membrane plate 22.

This also means that the atomizer will operate correctly even when the nebulizer is inclined. As such, a patient may use the atomizer with an increased ease of use, as he is much less restricted in the positioning of the nebulizer, as compared to the above discussed prior art devices.

Having described now the preferred embodiments of this invention, it will be apparent to one of skill in the art that other embodiments incorporating its concept may be used. It is felt, therefore, that this invention should not be limited to the disclosed embodiments, but rather should be limited only by the scope of the appended claims.

The invention claimed is:

1. A nebulizer comprising:

(A) a main body;

(B) an atomizer for atomizing a liquid so as to expel the liquid as a spray of droplets from the nebulizer; and (C) a vibrating element, wherein the atomizer comprises i. a substrate;

ii. a main recipient supported by the substrate for containing the liquid and having a bottom outer surface, a flat top inner surface and an outer wall erecting from the top surface to delimit the main recipient;

iii. a dosing reservoir arranged on the main recipient to delimit a specific predetermined amount of liquid to be expelled, and having an upper surface and a wall extending downwards from the upper surface towards the main recipient when assembled thereto, wherein the dosing reservoir is a disposable part and wherein the specific predetermined amount of liquid is contained in the dosing reservoir, wherein the size of the dosing reservoir defines the specific predetermined amount of liquid to be expelled, wherein the specific predetermined amount of liquid is predetermined for a specific treatment, and wherein the dosing reservoir comprises (a) a hollow section defining the predetermined amount of liquid, wherein the hollow section is delimited by the upper surface and by the wall that extends downwards from the upper surface;

(b) a solid section extending downwards from the upper surface;

(c) a central section that includes a hole traversing the upper surface and arranged in the solid section;

(d) an orifice membrane plate arranged at a bottom of the hole of the central section, for sealing the hole: and (e) a fluidic capillary channel arranged in-between a bottom surface of the solid section and the flat top inner surface of the main recipient to provide a capillary communication between the hollow section and the orifice membrane plate.

2. A nebulizer according to claim 1, wherein said dosing reservoir has a top sealing surface arranged above said fluidic capillary channel so that said fluidic capillary channel is trapped between said top inner surface and a top surface of the vibrating element.

3. A nebulizer according to claim 1, wherein said main recipient is provided as a disposable part.

4. A nebulizer according to claim 1, wherein said main body comprises electronic circuitry, said vibrating element, and a power source for powering said vibrating element so as to act on liquid in said atomizer, whereby said liquid is expelled as the spray of droplets.

5. A nebulizer according to claim 1, wherein said nebulizer includes said vibrating element, and said main body includes a power source for powering said vibrating element so as to act on liquid in said atomizer, whereby said liquid is expelled as a spray of droplets.

6. A nebulizer according to claim 2, wherein said main recipient is provided as a disposable part.

7. A nebulizer according to claim 2, wherein said main body comprises electronic circuitry, said vibrating element, and a power source for powering said vibrating element so as to act on liquid in said atomizer, whereby said liquid is expelled as the spray of droplets.

8. A nebulizer according to claim 3, wherein said main body comprises electronic circuitry, said vibrating element, and a power source for powering said vibrating element so as to act on liquid in said atomizer, whereby said liquid is expelled as the spray of droplets.

9. A nebulizer according to claim 2, wherein said main body comprises electronic circuitry, said vibrating element, and a power source for powering said vibrating element so as to act on liquid in said atomizer, whereby said liquid is expelled as the spray of droplets.

10. A nebulizer according to claim 6, wherein said main body comprises electronic circuitry, said vibrating element, and a power source for powering said vibrating element so as to act on liquid in said atomizer, whereby said liquid is expelled as the spray of droplets.

11. A nebulizer according to claim 2, wherein said nebulizer includes said vibrating element, and said main body includes a power source for powering said vibrating element so as to act on liquid in said atomizer, whereby said liquid is expelled as a spray of droplets.

12. A nebulizer according to claim 3, wherein said nebulizer includes said vibrating element, and said main body includes a power source for powering said vibrating element so as to act on liquid in said atomizer, whereby said liquid is expelled as a spray of droplets.

13. A nebulizer according to claim 6, wherein said nebulizer includes said vibrating element, and said main body includes a power source for powering said vibrating element so as to act on liquid in said atomizer, whereby said liquid is expelled as a spray of droplets.

14. A nebulizer according to claim 1, wherein a buffer zone is disposed in the main recipient between the wall of the dosing reservoir extending downwards from the upper surface and the outer wall of the main recipient.

* * * * *